United States Patent [19]

Seredenin et al.

[11] Patent Number: 5,378,846
[45] Date of Patent: Jan. 3, 1995

[54] 1,2,3,4-TETRAHYDROPYRROLO-[1,2-A]-PYRAZINE DERIVATIVES

[75] Inventors: Sergey B. Seredenin; Tatiana A. Voronina; Arkady M. Likhosherstov; Vitaly P. Peresada; Gennady M. Molodavkin, all of Moscow, U.S.S.R.; James A. Halikas, North Oaks, Minn.

[73] Assignee: Russian-American Institute For New Drug Development, Bloomington, Minn.

[21] Appl. No.: 75,641

[22] Filed: Jun. 11, 1993

[51] Int. Cl.⁶ .................. C07D 487/04; A61K 31/495
[52] U.S. Cl. ..................................... 544/349; 544/116
[58] Field of Search .............................. 544/116, 349; 514/233.2, 249

[56] References Cited

U.S. PATENT DOCUMENTS

| | | | |
|---|---|---|---|
| 4,188,389 | 2/1980 | Jirkovsky | 544/349 |
| 4,216,321 | 8/1980 | Skoldinov et al. | 544/349 |
| 4,230,856 | 10/1980 | Skoldinov et al. | 544/349 |

FOREIGN PATENT DOCUMENTS

| | | |
|---|---|---|
| 2010831 | 7/1979 | United Kingdom . |
| 2025936 | 1/1980 | United Kingdom . |
| 765268 | 9/1980 | U.S.S.R. . |
| 798104 | 1/1981 | U.S.S.R. . |

OTHER PUBLICATIONS

M. Abou-Gharbia, "Synthesis and Structure-Activity Relationship of Substituted Tetrahydro- and Hexahydro-1,2-benzisothiazol-3-one 1,1-Dioxides and Thiadiazinones: Potential Anxiolytic Agents", *J. Med. Chem.*, 32 1024–1033 (1989).

V. Persesada et al., "Azacycloalkanes. XXX. Pyrrolo [1,2-a] Pyrazines with Variable Degrees of Pyrazine Ring Saturation and Their Hypotensive Activity", *Pharmaceutical Chemistry Journal*, 21(9) 619–624 (1988). This is an English translation of the Russian-language article appearing in *Chem.-Pharmac. J.*, 21(9), 1054–1059 (1987).

V. Peresada et al., "Azacycloalkanes. XXXI: Arylalkylpyrolo(1,2-a)pyrazines and their effects on ischemized myocardium", *Pharmaceutical Chemistry Journal*, 22(10) 755–759 (1988). This is an English translation of the Russian-language article appearing in *Chem.-Pharmac. J.*, 22(10), 1193–1197 (1988).

*Primary Examiner*—Mark L. Berch
*Attorney, Agent, or Firm*—Merchant, Gould, Smith, Edell, Welter & Schmidt

[57] ABSTRACT

1,2,3,4-tetrahydropyrrolo[1,2-a]pyrazine derivatives having the formula (Formula I)

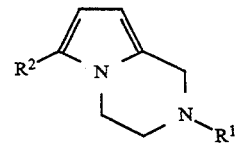

and therapeutically acceptable acid addition salts thereof (Formula I.HX), wherein: $R^1$=hydrogen or acyl groups; and $R^2$=hydrogen or substituted aminomethyl groups. Said compounds and their acid addition salts have psychotropic activity, particularly anxiolytic activity.

3 Claims, No Drawings

1,2,3,4-TETRAHYDROPYRROLO-[1,2-A]-PYRAZINE DERIVATIVES

FIELD OF THE INVENTION

The present invention relates to derivatives of 1,2,3,4-tetrahydropyrrolo-[1,2-a]-pyrazine. These compounds are useful as nonsedating antianxiety drugs.

BACKGROUND OF THE INVENTION

Antianxiety drugs, also known as anxiolytic drugs or tranquilizers, are increasingly important psychotropic drugs. They include the benzodiazepines, such as diazepam, chlordiazepoxide, gidazepam, oxazepam, phenazepam, lorazepam, and the like. These benzodiazepines have been the most widely used drugs for the treatment of anxiety. Other antianxiety drugs include, buspirone, gepirone, ipsapirone, and other drugs with high affinity and selectivity for $5HT_{1a}$ receptor sites. See for example, Abou-Gharbia et al., *J. Med. Chem.*, 32, 1024 (1989).

These agents have been very effective but there has been increasing concern about the disadvantages associated with benzodiazepine therapy. The spectrum of their pharmacological activity, in addition to anxiolytic activity, includes sedative, anticonvulsant, miorelaxant, and amnestic effects, which are often considered both unnecessary and undesirable in the treatment of pathological anxiety. Thus a substantial need exists for nontoxic, highly active, selectively anxiolytic drugs without sedative, muscle relaxant and amnestic activities, which can be used for the treatment of anxiety. The present invention is directed to addressing this need.

A number of compounds having 1,2,3,4-tetrahydropyrrolo-[1,2-a]-pyrazine heterocycle have been reported. For example, nonsubstituted 1,2,3,4-tetrahydropyrrolo-[1,2-a]-pyrazine is described by A. Skoldinov et al. (U.S. Pat. No. 4,230,856 issued Oct. 28, 1980; USSR Patent No. 798,104 published Jan. 25, 1981). This compound is a precursor in the synthesis of octahydropyrrolo-[1,2-a]-pyrazine, which is useful for the synthesis of physiologically active drugs. 1- and 1,2-substituted 1,2,3,4-tetrahydropyrrolo-[1,2-a]-pyrazine derivatives, having antidepressant activity, are described by I. Jirkovsky (U.S. Pat. No. 4,188,389 issued Feb. 12, 1980). 1-substituted 1,2,3,4-tetrahydropyrrolo-[1,2-a]-pyrazines, having hypotensive activity, are described by V. Peresada et al., *Khim-Farm. Zh.*, 21(9), 1054 (1987). 1-substituted 1,2,3,4-tetrahydropyrrolo-[1,2-a]-pyrazines, possessing coronary-dilating activity, are described by V. Peresada et al., *Khim-Farm. Zh.*, 22(10), 1193 (1988).

SUMMARY OF THE INVENTION

The present invention relates to derivatives of 1,2,3,4-tetrahydropyrrolo-[1,2-a]-pyrazine and their salts. These compounds are useful as selective antianxiety drugs. More specifically, the present invention relates to 1,2,3,4-tetrahydropyrrolo-[1,2-a]-pyrazine derivatives, having hydrogen or acyl groups at position 2 of the heterocycle and hydrogen or substituted aminomethyl groups at position 6. The present invention also relates to the acid addition salts of said compounds, preferably salts of succinic, oxalic, and maleic acids. These 1,2,3,4-tetrahydropyrrolo-[1,2-a]-pyrazine derivatives and therapeutically acceptable acid addition salts thereof are useful as selective anxiolytics agents without myorelaxant and amnestic effects. 1,2,3,4-tetrahydropyrrolo-[1,2-a]-pyrazine succinate is a particularly effective anxiolytic agent.

The present invention provides derivatives of 1,2,3,4-tetrahydropyrrolo-[1,2-a]-pyrazine having the following structural formula (Formula I):

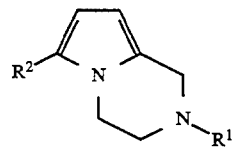

wherein $R^1$ is hydrogen, an acetyl (—C(O)CH₃) group, or a benzoyl (—C(O)C₆H₅) group; and $R^2$ is hydrogen, a dimethylaminomethyl (—CH₂N(CH₃)₂) group, a piperidinomethyl

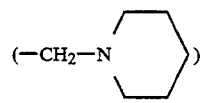

group, or a morpholinomethyl

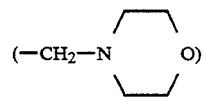

group. Therapeutically acceptable acid addition salts of compounds of Formula I are also within the scope of the present invention (Formula I.HX):

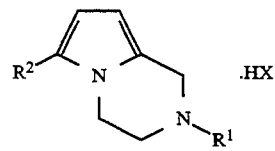

wherein $R^1$ and $R^2$ are as described for Formula I. For the compounds of Formula I, $R^1$ and $R^2$ cannot both be hydrogen; however, for the compounds of Formula I.HX, $R^1$ and $R^2$ can both be hydrogen.

The compounds of Formula I and therapeutically acceptable acid addition salts thereof (Formula I.HX) can be prepared from 1,2,3,4-tetrahydropyrrolo-[1,2-a]-pyrazine. For example, 1,2,3,4-tetrahydropyrrolo-[1,2-a]-pyrazine reacts with succinic acid to produce 1,2,3,4-tetrahydropyrrolo-[1,2-a]-pyrazine hydrosuccinate. Acylating 1,2,3,4-tetrahydropyrrolo-[1,2-a]-pyrazine by acetic anhydride or benzoyl chloride results in the corresponding 2-acyl derivatives of tetrahydropyrrolo-[1,2-a]-pyrazine of the following formula (Formula II):

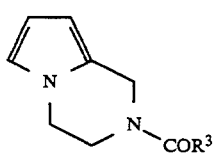

wherein $R^3$ is —CH₃ or —C₆H₅. Reacting 2-acyl derivatives according to Formula II with dimethylamino piperidine or morpholine hydrochloride, compounds of Formula I can be obtained, wherein $R^1$ is an acetyl or a benzoyl group, and $R^2$ is a dimethylaminomethyl, a piperidinomethyl, or a morpholinomethyl group. Finally, reacting these bases with oxalic acid, the corresponding hydrooxalates can be obtained.

The compounds of Formula I and the acid addition salts of Formula I.HX have psychotropic activity, especially anxiolytic effect. The most preferred compound, namely 1,2,3,4-tetrahydropyrrolo-[1,2-a]-pyrazine hydrosuccinate of the following formula (Formula III) is particularly useful as an anxiolytic agent.

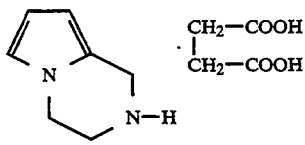

The compounds of Formula I and the acid addition salts of Formula I.HX are useful for treating anxiety and anxiety bound disorders in mammals, e.g., humans. Accordingly, an effective anxiolytic amount of a compound of Formula I, or a therapeutically acceptable acid addition salt Formula I.HX is administered to said mammal. The compound of Formula I, or a therapeutically acceptable acid addition salt of Formula I.HX, and a pharmaceutically acceptable carrier also form a useful pharmaceutical composition for treating anxiety or anxiety bound disorders in mammals.

DETAILED DESCRIPTION OF THE INVENTION

The compounds of the present invention are selective anxiolytic, i.e., antianxiety, drugs with substantially no sedative or myorelaxing side effects. They also have a pronounced anti-amnestic effect, as can be evidenced by a passive avoidance test disrupted by electrical shock. Furthermore, they display an anti-hypoxic effect, as evidenced by a hypobaric hypoxia test wherein the survival rate improved. Unlike traditional benzodiazepine tranquilizers, the compounds of the present invention generally have substantially no anti-seizure activity and also do not typically deteriorate learning or memory.

The compounds of the present invention are derivatives of 1,2,3,4-tetrahydropyrrolo-[1,2-a]-pyrazine having the following structural formula (Formula I):

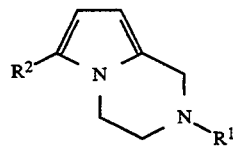

wherein $R^1$ is hydrogen, an acetyl or a benzoyl group; and $R^2$ is hydrogen, a dimethylaminomethyl, a piperidinomethyl, or a morpholinomethyl group, with the proviso that $R^1$ and $R^2$ are not both hydrogen. Therapeutically acceptable acid addition salts of such compounds are also within the scope of the present invention. For the acid addition salts, however, $R^1$ and $R^2$ can both be hydrogen. Thus, compounds of the present invention also include derivatives of 1,2,3,4-tetrahydropyrrolo-[1,2-a]-pyrazine having the following formula (Formula I.HX):

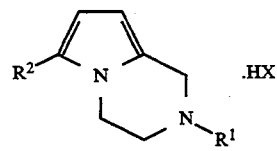

wherein $R^1$ is hydrogen, an acetyl group, or a benzoyl group; $R^2$ is hydrogen, a dimethylaminomethyl group, a piperidinomethyl group, or a morpholinomethyl group; and HX is a therapeutically acceptable acid. Thus, as used herein, "derivatives of 1,2,3,4-tetrahydropyrrolo-[1,2-a]-pyrazine" include 2-, and 2,6-substituted derivatives, as well as acid addition salts of 1,2,3,4-tetrahydropyrrolo-[1,2-a]-pyrazine and 2-, and 2,6-substituted derivatives of 1,2,3,4-tetrahydropyrrolo-[1,2-a]-pyrazine.

Examples of suitable acids include: mineral acids, such as hydrochloric acid and the like; organic acids, such as oxalic acid, maleic acid, succinic acid, and the like; and acids that are sparingly soluble in body fluids and impart slow release properties to the salts such as pamoic acid and the like.

Preferably, the therapeutically acceptable acid (HX) is an organic acid. Of the therapeutically acceptable organic acids, the preferred acids are maleic, succinic, and oxalic acid. More preferably, the acid is succinic or oxalic acid. and most preferably it is succinic acid. The therapeutically acceptable acid addition salts of Formula I.HX are prepared by reacting the base form of 1,2,3,4-tetrahydropyrrolo-[1,2-a]-pyrazine or a substituted 1,2,3,4-tetrahydropyrrolo-[1,2-a]-pyrazine with one or more equivalents, preferably with an excess, of the appropriate acid in an organic solvent, such as ethanol for example.

These compounds can be prepared as outlined in the following scheme.

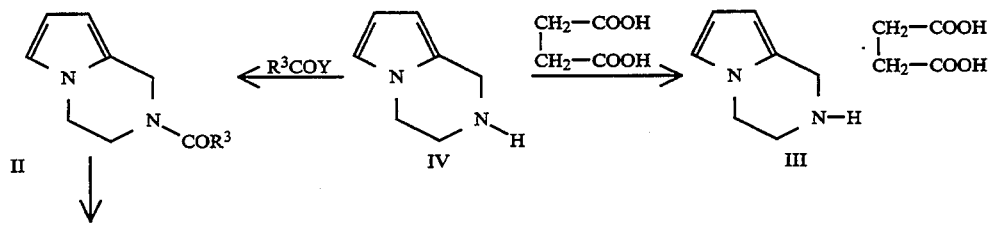

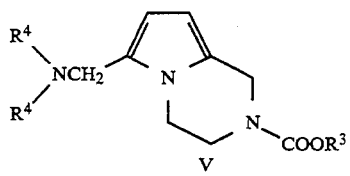 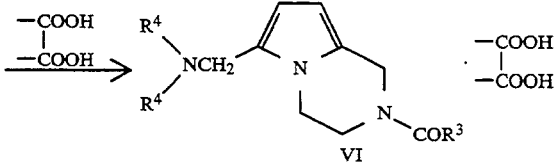

wherein
Y is —Cl or —C(O)OCH₃
R³ is —CH₃ or —C₆H₅
R⁴ is —CH₃

can also be

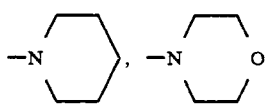

A precursor of the synthesis of compounds of Formula I and Formula I.HX is 1,2,3,4-tetrahydropyrrolo-[1,2-a]-pyrazine (see U.S. Pat. No. 4,230,856), which is obtained by means of reduction of 3,4-dihydropyrrolo-[1,2-a]-pyrazine (see U.S. Pat. No. 4,216,321). Tetrahydropyrrolo-[1,2-a]-pyrazine (IV) reacts with an ethanol solution of succinic acid to form 1,2,3,4-tetrahydropyrrolo-[1,2-a]-pyrazine hydrosuccinate (III). 2-Acetyl-1,2,3,4-tetrahydropyrrolo-[1,2-a]-pyrazine (II, R³=—CH₃) and 2-benzoyl-1,2,3,4-tetrahydropyrrolo-[1,2-a]-pyrazine (II, R³=—C₆H₅) are obtained by reacting the bicyclic compound (IV) with acetic anhydride or benzoyl chloride, respectively, in benzene solution. The 2-acyl derivatives (II) react with dimethylamine, piperidine or morpholine hydrochlorides and a 40% solution of formaldehyde at room temperature to form the corresponding 2-acyl-6-amino derivatives of 1,2,3,4-tetrahydropyrrolo-[1,2-a]-pyrazine (V). Reacting ethanol solutions of these bases (V) with ethanol solutions of oxalic acid results in the formation of the corresponding hydrooxalates (VI).

The dosage of the compounds of the present invention as anxiolytic agents varies with the patient, form of administration, and the particular compound chosen. Generally, the compounds are administered in an amount that affords effective results without causing harmful or deleterious side effects. Preferably and advantageously, the compounds of the present invention have a pronounced and selected anxiolytic effect at a dosage level of about 0.5 mg/kg to about 5.0 mg/kg, as measured by the Vogel Conflict test (Vogel et al., *Psychopharmacologia*, 21, 1–7 (1971); J. E. Barrett in *Animal Models in Psychopharmacology., Advances in Pharmacological Sciences*, Birkhauser Verlag, Basel, p. 37–52 (1991); and Molodavkin et al., *Exper. Clin. Pharmacol.*, 56, (1993)). Thus, the magnitude of the anxiolytic effect of the compounds of the present invention is superior to that of diazepam and alprozalam, and it is comparable to that of lorazepam. At these low doses, and even at higher doses, such as 250 mg/kg, the compounds of the present invention do not generally display any significant amount of sedation or myorelaxation. Furthermore, toxicity of these substances is generally low, i.e., the LD₅₀ is no greater than about 1500 mg/kg. Some of these compounds are able to decrease the locomotor activity (Example 11), and effect the duration of immobility in a behavioural despair test (Example 12).

Compound 1 (1,2,3,4-tetrahydropyrrolo-[1,2-a]-pyrazine hydrosuccinate, see Table 1 ) was chosen for detailed study because of its excellent anxiolytic activity and low toxicity (Example 13). Compound 1, unlike known anxiolytic agents (for example, benzodiazepines), does not manifest amnestic and myorelaxant effects and possesses selective anxiolytic activity. This compound can increase the amount of punished responses in a Vogel conflict test after acute and chronic administration (Examples 10), increase the threshold of aggressive response (Example 14), and increase the duration of animals' survival after pentylenetetrazole injection (Example 15).

In contrast to benzodiazepine anxiolytics, Compound 1 does not change the duration of immobility in a behavioral despair test (Example 12). Compound 1 produces activating (anxiolytic) effect in initially low active BALB/c mice (Example 16) in an "open field" test. In contrast to benzodiazepine tranquilizers. Compound 1 in an anxiolytic dose range does not cause sedation in C57B1/6 mice, initially active in an "open field" test. Unlike benzodiazepine anxiolytics, Compound 1 is able to facilitate memory trace formation (Example 17). In contrast to known anxiolytic drugs, Compound 1 fails to evoke disturbances in the coordination of movements and myorelaxation (Example 18). Compound 1 also has low toxicity (Example 13).

The present invention is also directed to various methods of treating suffering humans by means of administering an effective dose of the compounds of the invention. Such methods include treating humans suffering from generalized anxiety disorder, atypical anxiety disorder, panic disorder, anticipatory anxiety, post-traumatic anxiety, adjustment disorder with anxious mood, somatic disorders; and also many other nonpsychotic anxiety reactions such as anxiety in cancer patients or anxiety present with or triggered by many physical illnesses.

The compounds of Formula I and Formula I.HX can be used alone or in combination with other active ingredients and solid or liquid inert carriers in pharmaceutical compositions. They can be administered orally or parenterally. These compositions can be in the form of tablets, capsules, elixirs, suspensions, parenterals, and the like.

Tablets can contain the active ingredient in admixture with nontoxic pharmaceutical excipients known to be suitable in the manufacture of tablets. Suitable pharmaceutical excipients include, for example, starch, milk and sugar. The tablets can be uncoated or they can be coated by known techniques so as to delay disintegration and absorption in the gastrointestinal tract and thereby provide a sustained action over a longer period. Aqueous suspensions can contain the active ingredient in admixture with one or more nontoxic pharmaceutical excipients known to be suitable in the manufacture of aqueous suspensions. Suitable excipients include, for example, methyl-cellulose, sodium alginate, gum acacia, and lecithin. The aqueous suspensions can also contain one or more preservatives, and one or more coloring, flavoring, or sweetening agents. Nonaqueous suspensions can be formulated by suspending the active ingredient in a vegetable oil, such as, for example, olive oil, sesame oil, or coconut oil, or in a mineral oil. The suspension can contain a thickening agent, such as beeswax, a sweetening agent, flavoring agent, or antioxidant.

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention.

EXAMPLE 1

1,2,3,4-Tetrahydropyrrolo-[1,2-a]-Pyrazine Hydrosuccinate

Into a 0.5 liter single-neck flask provided with a magnetic stirrer was charged 36 g of 3,4-dihydropyrrolo-[1,2-a]-pyrazine, 250 ml of absolute methanol, and 1 g of a 10% Pd/BaSO$_4$. The flask was then connected with a supply of hydrogen. To remove air, the reaction mass was purged with hydrogen and then allowed to stir under the hydrogen atmosphere until the theoretical amount of hydrogen was absorbed, i.e., for about 3 hours. The catalyst was removed from the resultant reaction mixture by filtration. The solvent was removed by distillation, the residue was distilled under vacuum, and the fraction with a boiling point of 100°–101° C. at 7 mm Hg was collected. The yield of 1,2,3,4-tetrahydropyrrolo-[1,2-a]-pyrazine was 34 g (95% of theoretical); $n_D^{20}$ was 1.5530. Anal. calculated for $C_7H_{10}N_2$: C 68.2%; H 8.25%; N 22.93% and found: C 68.49%; H 8.15%; N 22.86%.

3.66 g of 1,2,3,4-tetrahydropyrrolo-[1,2-a]-pyrazine was added to a solution of 3.9 g of succinic acid in 20 ml of ethanol. The precipitate is filtered and crystallized from ethanol. The yield of the title compound was 5.5 g (76.3%). The melting point 152°–153° C. Anal. calculated for $C_7H_{10}N_2.C_4H_6O_4$: C 54.99%; H 6.71%; N 11.66% and found: C 55.27%; H 6.77%; N 11.73%.

EXAMPLE 2

2-Acetyl-1,2,3,4-Tetrahydropyrrolo-[1,2,-a]-pyrazine

To a solution of 12.2 g 1,2,3,4-tetrahydropyrrolo-[1,2,-a]-pyrazine in 40 ml of anhydrous benzene was added 15.3 g of acetic anhydride in small portions. The reaction mixture was kept for 3 hours at room temperature. Then the reaction mass was poured into water, the organic phase was separated and washed with a 5% solution of sodium carbonate, and then water. The solvent was removed by distillation, the residue was distilled under vacuum, and the fraction with a boiling point of 146°–147° C. at 2 mm Hg was collected. The yield of the title compound was 14 g (86%). Nmr (CDCl$_3$): δ2.0 (s) (3H,CH$_3$); 3.6–4.0 (m) (4H, 3,4-CH$_2$); 4.6 (s) (2H, 1-CH$_2$); 5.7–5.9 (m) (1H, 7-H); 5.9–6.06 (m) (1H, 8-H); 6.38–6.5 (m) (1H, 6-H). Anal. calculated for $C_9H_{12}N_2O$: C 65.38%; H 7.37%; N 17.01% and found: C 65.62%: H 7.32%; N 17.00%.

EXAMPLE 3

2-Acetyl-6-(Dimethylaminomethyl)-1,2,3,4-Tetrahydropyrrolo-[1,2-a]-Pyrazine

A mixture of 1.35 g of dimethylammonium chloride, 1.24 g of a 40% solution of formaldehyde, and 2.45 g of 2-acetyl-1,2,3,4-tetrahydropyrrolo-[1,2-a]-pyrazine was stirred for 4 hours at room temperature. 10 ml of water, alkalized with a 25% solution of ammonia, was added to the reaction mass and the product was extracted with benzene. Benzene was removed by distillation and the residue was distilled under vacuum to give 1.7 g (51.5%) of the title compound. The boiling point was 177°–178° C. at 1 mm Hg. Nmr (CDCl$_3$): δ2.23 (s) (9H, CH$_3$); 3.38 (s) (2H, CH$_2$N); 3.8–4.2 (m) (4H, 3,4-CH$_2$); 4.7 (s) (2H, 1-CH$_2$); 5.8–5.95 (m) (1H, 7-H); 5.95–6.1 (m) (1H, 8-H). Anal. calculated for $C_{12}H_{19}N_3O$: C 65.13%; H 8.65%; N 18.99%; and found: C 65.36%; H 8.76%; N 19.21%.

The hydrooxalate of 2-acetyl-6-(dimethylaminomethyl)-1,2,3,4-tetrahydropyrrolo-[1,2-a]-pyrazine was prepared by combining solutions of 2.29 g of the title compound in 5 ml of ethanol and a solution 1.39 g of oxalic acid in 5 ml of ethanol. The precipitate was filtered off and crystallized from ethanol. The yield of the title compound hydrooxalate was 1.8 g (58%); mp=128°–129° C. Anal. calculated for $C_{12}H_{19}N_3O.C_2H_2O_4$: C 54.01%; H 6.8%; N 13.5% and found: C 54.17%; H 6.88%; N 13.24%.

EXAMPLE 4

2-Acetyl-6-(Piperidinomethyl)-1,2,3,4-Tetrahydropyrrolo-[1,2-]-Pyrazine

A mixture of 2.2 g of piperidine hydrochloride, 1.24 g of a 40% solution of formaldehyde, and 2.45 g of 2-acetyl-1,2,3,4-tetrahydropyrrolo-[1,2-a]-pyrazine was stirred for 4 hours at room temperature. 10 ml of water, alkalized with 25% solution of ammonia, was added to the reaction mass and the product was extracted with benzene. Benzene was removed by distillation and the residue was crystallized from ethanol to give 2.5 g (64%) of the title compound, mp 114°–115° C. Nmr (CDCl$_3$): δ1.3–1.6 (m) (6H, CH$_2$); 2.1 (s) (3H, CH$_3$); 2.0–2.4 (m) (4H, CH$_2$); 3.3 (s) (2H, CH$_2$N); 3.7–4.1 (m) (4H, 3,4-CH$_2$); 4.6 (s) (2H, 1-CH$_2$); 5.7–5.82 (m) (1H, 7-H); 5.82–5.98 (m) (1H, 8-H). Anal. calculated for $C_{15}H_{23}N_3O$: C 68.93%; H 8.87%; N 16.08% and found: C 69.09%; H 8.82%; N 15.95%.

In the same manner as described in Example 3 the title compound hydrooxalate was obtained. The melting point was 114°–115° C. Anal. calculated for $C_{15}H_{23}N_3O.C_2H_2O_4$: C 58.10%, H 7.17%, N 11.96% and found: C58.10%, H7.17%, N 11.96%.

EXAMPLE 5

2-Acetyl-6-(Morpholinomethyl)-1,2,3,4-Tetrahydropyrrolo-[1,2-a]-Pyrazine

A mixture of 2.72 g of morpholine hydrochloride, 1.65 g of a 40% solution of formaldehyde, and 3.3 g of 2-acetyl-1,2,3,4-tetrahydropyrrolo-[1,2-a]-pyrazine was stirred for 4 hours at room temperature. 15 ml of water, alkalized with a 25% solution of ammonia, was added to the reaction mass and the product was extracted with benzene. Benzene was removed by distillation and the residue was crystallized from ethanol to give 3.2 g (61%) the title compound, mp 117°–118° C. Nmr (CDCl$_3$): δ2.1 (s) (3H, CH$_3$); 2.2–2.4 (m) (4H, CH$_2$); 3.38 (s) (2H, CH$_2$-N); 3.5–3.7 (m) (4H, CH$_2$), 3.7–4.1 (m) (4H, 3,4-CH$_2$); 4.6 (s) (2H, 1-CH$_2$); 5.7–5.82 (m) (1H, 7-H); 5.82–6.0 (m) (1H, 8-H). Anal. calculated for C$_{14}$H$_{21}$N$_3$O$_2$: C 63.85%; H 8.04%; N 15.96% and found: C 63.90%; H 8.06%; N 15.76%.

In the same manner as described in Example 3 the title compound hydrooxalate was obtained. The melting point was 135°–136° C. Anal. calculated for C$_{14}$H$_{21}$N$_3$O$_2$.C$_2$H$_2$O$_4$: C 54.38%; H 6.56%; N 11.89% and found C 54.13%; H 6.45%; N 11.73%.

EXAMPLE 6

2-Benzoyl-1,2,3,4-Tetrahydropyrrolo-[1,2-a]-Pyrazine

To a solution of 12.2 g of 1,2,3,4-tetrahydropyrrolo-[1,2-a]-pyrazine and 22.2 g of triethylamine in 50 ml of anhydrous benzene, 15.4 g of benzoyl chloride was added in small portions at 10°–15° C. The reaction mass was stirred for 3 hours at room temperature and then poured into water. The organic phase was separated, and washed with a 5% solution of sodium carbonate and then water. The solvent was removed by distillation, the residue was distilled under vacuum, and the fraction with a boiling point of 189°–191° C. at 1 mm Hg was collected. The yield of the title compound was 15 g (66.5%). Nmr (CDCl$_3$): δ3.7–3.9 (m) (4H, 3,4-CH$_2$); 4.58 (s) (2H, 1-CH$_2$); 5.6–5.8 (m) (1H, 7-H); 5.8–6.0 (m) (1H, 8-H); 6.2–6.4 (m) (1H, 6-H); 7.2–7.4 (m) (5H-C$_6$H$_5$). Anal. calculated for C$_{14}$H$_{14}$N$_2$O: C 74.31%; H 6.24%; N 12.38% and found: C 74.21%; H 6.24%; N 12.45%.

EXAMPLE 7

2-Benzoyl-6-(Dimethylaminomethyl)-1,2,3,4-Tetrahydropyrrolo-[1,2-]-Pyrazine

A mixture of 0.9 g of dimethylammonium chloride, 0.83 g of a 40% solution of formaldehyde, and 2.26 g of 2-benzoyl-1,2,3,4-tetrahydropyrrolo-[1,2-a]-pyrazine was stirred for 4 hours at room temperature. 10 ml of water, alkalized with 25% solution of ammonia, was added to the reaction mass and the product was extracted with benzene. Benzene was removed by distillation and the residue was crystallized from ethanol to give 1.8 g (63.3%) of the title compound: mp=108°–109° C. Nmr (CDCl$_3$): δ2.1 (s) (6H, CH$_3$); 3.25 (s) (2H, CH$_2$N); 3.7–4.1 (m) (4H, 3,4-CH$_2$); 4.68 (s) (2H, 1-CH$_2$); 5.6–5.8 (m) (1H, 7H); 5.8–6.0 (m) (1H, 8-H); 7.2–7.4 (5H, —C$_6$H$_5$). Anal. calculated for C$_{17}$H$_{21}$N$_3$O: C 72.05%; H 7.47%; N 14.83% and found: C 72.18%; H 7.47%; N 14.91%.

The hydrooxalate was prepared by combining a solution of 2.83 g of the title compound in 10 ml of ethanol and a solution of 1.39 g of oxalic acid in 5 ml of ethanol. The precipitate was filtered off and recrystallized from ethanol. The yield of the title compound hydrooxalate was 2.4 g (64.5%), mp:32 159°–160° C. Anal. calculated for C$_{17}$H$_{21}$N$_3$O.C$_2$H$_2$O$_4$: C 61.11%; H 6.21%; N 11.25% and found: C 60.82%; H 6.18%; N 11.32%.

EXAMPLE 8

2-Benzoyl-6-(Piperidinomethyl)-1,2,3,4-Tetrahydropyrrolo-[1,2-a]-Pyrazine Hydrooxalate A mixture of 1.33 g of piperidine hydrochloride, 0.83 g of a 40% solution of formaldehyde, and 2.26 g of 2-benzoyl-1,2,3,4-tetrahydropyrrolo-[1,2-a]-pyrazine was stirred for 4 hours at room temperature. 10 ml of water, alkalized with a 25% solution of ammonia, was added to the reaction mass and the product was extracted with benzene. The benzene solution was filtered through a column of aluminum oxide, and the benzene was removed by distillation to give 2.1 g (65%) of 2-benzoyl-6-(piperidinomethyl)-1,2,3,4-tetraydropyrrolo[1,2-a]pyrazine. This compound was prepared in the form of a noncrystalline oil. Nmr (CDCl$_3$): δ1.3–1.6 (m) (6H, CH$_2$); 2.1–2.4 (m) (4H, CH$_2$); 3.3 (s) (2H, CH$_2$N); 3.7–4.2 (m) (4H, 3,4-CH$_2$); 4.64 (s) (2H, 1-CH$_2$); 5.54–5.68 (m) (1H, 7-H); 5.7–5.8 (m) (1H, 8-H); 7.3–7.4 (m) (5H, C$_6$H$_5$). Anal. calculated for C$_{20}$H$_{25}$N$_3$O: C 74.27%; H 7.79%; N 12.99% and found: C 74.35%; H 7.63%; N 12.83%.

The title compound was prepared from 2-benzoyl-6-(piperidinomethyl)-1,2,3,4-tetrahydropyrrolo-[1,2-a]-pyrazine and aa equimolar amount of oxalic acid by means of the procedure described in Example 3. The yield was 71.3%; mp=95°–96° C. Anal. calculated for C$_{20}$H$_{25}$N$_3$O.C$_2$H$_2$O$_4$: C 63.91%; H 6.58%; N 10.16% and found: C 63.69%; H 6.80%; N 10.08%.

EXAMPLE 9

2-Benzoyl-6-(Morpholinomethyl)-1,2,3,4-Tetrahydropyrrolo-[1,2-a]-Pyrazine Hydrooxalate A mixture of 2.05 g of morpholine hydrochloride, 1.24 g of a 40% solution of formaldehyde, and 3.4 g of 2-benzoyl-1,2,3,4-tetrahydropyrrolo-[1,2-a]-pyrazine was stirred for 4 hours at room temperature. 10 ml of water, alkalized with a 25% solution of ammonia, was added to the reaction mass and the product was extracted with benzene. The benzene solution was filtered through a column of aluminium oxide and the benzene was removed by distillation to give 2.2 g (67.5%) of 2-benzoyl-6-(morpholinomethyl)-1,2,3,4-tetrahydropyrrolo[1,2-a]pyrazine. This compound was prepared in the form of a noncrystalline oil. Nmr (CDCl$_3$): δ2.1–2.4 (m) (4H, CH$_2$); 3.3 (s) (2H, CH$_2$N); 3.5–3.6 (m) (4H, CH$_2$); 3.7–4.0 (m) (4H, 3,4-CH$_2$); 4.6 (s) (2H, 1-CH$_2$); 5.6–5.7 (m) (1H, 7-H); 5.8–5.9 (m) 1H, 8H); 7.3–7.4 (5H, C$_6$H$_5$). Anal. calculated for C$_{19}$H$_{23}$N$_3$O$_2$: C 70.13%; H 7.12%; N 12.91% and found: C 70.36%; H 7.19%; N 12.75%.

The title compound was prepared from 2-benzoyl-6-(morpholinomethyl)-1,2,3,4-tetrahydropyrrolo-[1,2-a]-pyrazine and an equimolar amount of oxalic acid by means of the procedure described in Example 3. The yield was 64.5%, mp=101°–102° C. Anal. calculated for C$_{19}$H$_{23}$N$_3$O$_2$.C$_2$H$_2$O$_4$: C 60.71%; H 6.07%; N 10.11% and found: C 60.51%; H 6.20%; N 9.87%.

EXAMPLE 10

Anxiolytic Activity

Compounds according to the present invention were checked for their anxiolytic activity. Behaviour suppressed by punishment is a very reliable indicator of the anxiolytic activity of drugs. A variant of the conflict situation test was used to reveal anxiety in water-deprived rats whose licking was suppressed by shock (see Vogel et al., *Phychopharmacologia*, 21, 1–7 (1971); J. E. Barrett in *Animal Models in Psychopharmacology, Advances in Pharmacological Sciences*, 1991; and Birkhauser Verlag, Basel, p. 37.52, Molodavkin et al., *Exper. Clin. Pharmacol.*, 56, (1993), which are incorporated herein by reference).

The experiments were carried out using outbred male albino rats (180–220 g). This experiment involved previous training of water-deprived rats to drink water from a trough. Next day electrical stimulation was given delivering 0.5 mA electric shocks through the trough and metal grid floor of the experimental chamber. A conflict situation was created by clashing motivations (survival and self defense). The degree of anxiolytic activity was estimated by the measurement of the amount of punished licks for 10 min. Each compound was administered intraperitoneally 45 min. before the conflict test.

The compounds of the present invention caused a pronounced anxiolytic effect. Most of them increased values of the punished responses (Table 1). Compound 1 in a dosage range of 0.5–2 mg/kg displayed more anxiolytic effect than diazepam did when injected in doses of 1 and 2 mg/kg in the conflict test (Table 2).

It was shown that anxiolytic effectiveness of Compound 1 is preserved after its chronic administration (5 mg/kg intraperitoneally (i.p.) once daily for 40 days), (Table 3).

TABLE 1

The influence of compounds (2.0 mg/kg, i.p.) on rat behavior in Vogel conflict test

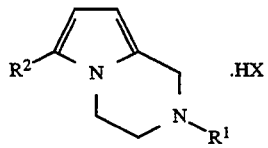

| Compound | $R^1$ | $R^2$ | HX | The number of punished responses |
|---|---|---|---|---|
| Control (saline) | | | | 14.0 ± 5.72 |
| 1 | H | H | HOOC(CH$_2$)$_2$COOH | 43.52 ± 14.8$^a$ |
| 2 | —COCH$_3$ | —CH$_2$N(CH$_2$)$_2$ | HOOCCOOH | 63.00 ± 35.38$^a$ |
| 3 | —COCH$_3$ | —CH$_2$—N⟨piperidine⟩ | HOOCCOOH | 22.00 ± 4.86 |
| 4 | —COCH$_3$ | —CH$_2$—N⟨morpholine⟩ | HOOCCOOH | 9.25 ± 1.75 |
| 5 | —COC$_6$H$_5$ | —CH$_2$N(CH$_3$)$_2$ | HOOCCOOH | 85.25 ± 32.04$^a$ |
| 6 | —COC$_6$H$_5$ | —CH$_2$—N⟨piperidine⟩ | HOOCCOOH | 30.75 ± 13.17 |
| 7 | —COC$_6$H$_5$ | —CH$_2$—N⟨morpholine⟩ | HOOCCOOH | 25.00 ± 5.99 |

$^a$P < 0.05 compared to control

TABLE 2

Dose-response relationship for Compound 1 revealed in Vogel conflict test

| Compound | Dose mg/kg | The number of punished responses |
|---|---|---|
| Control | — | 14.0 ± 5.72 |
| (saline) | | |
| Compound 1 | 0.25 | 29.38 ± 12.54 |
| — | 0.5 | 49.88 ± 19.27$^a$ |
| — | 1.0 | 41.29 ± 16.71$^a$ |
| — | 2.0 | 43.52 ± 14.8$^a$ |
| — | 5.0 | 29.88 ± 13.13 |
| — | 10.0 | 30.88 ± 10.93$^a$ |
| Diazepam | 1.0 | 22.25 ± 10.89 |
| — | 2.0 | 47.25 ± 22.49$^a$ |

$^a$P < 0.05 compared to control

TABLE 3

Anxiolytic effect of Compound 1 after acute and chronic administration in Vogel conflict test

| Groups | Compound, dose (mg/kg) | The number of punished responses |
|---|---|---|
| Acute administration | Control (saline) | 12.76 ± 6.39 |
| | Compound 1 (5 mg/kg) | 49.52 ± 15.91$^a$ |
| Chronic administration (once daily for 40 days) | Control (saline) | 24.3 ± 4.8 |
| | Compound 1 (5 mg/kg) | 85.8 ± 6.7$^b$ |

$^a$P < 0.05 compared to control
$^b$P < 0.01 compared to control

EXAMPLE 11

Locomotor Activity

Compounds according to the present invention were checked for their influence on gross behaviour. The experiments described herein (Examples 11, 12, 13, 14, and 15) were carried out using outbred male mice weighing approximately 18-24 g. Each substance was administered intraperitoneally 45 min. before the experiment. Locomotor activity was estimated individually for each animal for 3 min. using an actometer 'Era-1' (Russia).

Compounds 2, 3, and 7 were demonstrated to decrease locomotor activity. Compound 1 in the dose range of 0.1-0.3 mg/kg i.p. neither stimulated nor depressed the spontaneous motor activity (Table 4).

TABLE 4

Influence of compounds on the locomotor activity in mice

| Substance | Dose, mg/kg | The number of movements for 3 min. | |
|---|---|---|---|
| | | Horizontal activity | Vertical activity |
| Control | — | 627.0 ± 9.2 | 21.3 ± 2.2 |
| Compound 1 | 0.1 | 650.8 ± 12.5 | 24.7 ± 2.5 |
| | 0.3 | 657.7 ± 15.5 | 25.2 ± 4.1 |
| Control | — | 590.6 ± 23.1 | 28.6 ± 4.7 |
| Compound 2 | 10.0 | 524.4 ± 36.9 | 10.0 ± 2.1$^a$ |
| | 20.0 | 489.1 ± 9.7$^a$ | 22.4 ± 3.0 |
| Control | — | 636.3 ± 21.0 | 22.4 ± 4.8 |
| Compound 3 | 10.0 | 532.5 ± 42.1 | 8.1 ± 1.9$^a$ |
| | 20.0 | 442.7 ± 30.3$^a$ | 9.2 ± 4.4$^a$ |
| Control | — | 626.1 ± 6.7 | 25.9 ± 5.0 |
| Compound 4 | 10.0 | 479.6 ± 22.8$^a$ | 17.6 ± 6.9 |
| | 20.0 | 564.5 ± 22.5$^a$ | 24.7 ± 5.6 |
| Control | — | 586.3 ± 19.7 | 24.2 ± 7.9 |
| Compound 5 | 10.0 | 676.1 ± 34.5$^a$ | 36.1 ± 5.8 |
| | 20.0 | 659.7 ± 32.7 | 36.6 ± 8.6 |
| Control | — | 556.5 ± 27.5 | 22.1 ± 7.1 |
| Compound 6 | 10.0 | 693.0 ± 25.3 | 16.5 ± 6.2$^a$ |
| | 20.0 | 644.0 ± 30.4 | 19.9 ± 3.4 |
| Control | — | 491.7 ± 19.3 | 35.0 ± 8.1 |
| Compound 7 | 10.0 | 475.1 ± 11.2$^a$ | 13.7 ± 2.5$^a$ |
| | 20.0 | 474.0 ± 14.7$^a$ | 12.4 ± 3.8$^a$ |

$^a$P < 0.05 compared to control

EXAMPLE 12

Behavioral Despair

The influence of compounds on behavioral despair was studied according to the model described by Porsolt et al., *Arch. int. pharmacodyn.et ther.*, 228, 327-326 (1977), which is incorporated herein by reference. Mice, when forced to swim in a cylinder of water without the possibility of escape, rapidly adopt a characteristic immobile posture. They do not make any further attempts to escape. The only movements they make are those necessary to keep their heads above water.

Compounds 5 and 6 reduced the duration of immobility induced by forced swimming. Compounds 2 and 3 increased the duration of immobility. Compounds 1, 4, and 7 did not show any activity in this paradigm (Table 5).

TABLE 5

The influence of compounds on the duration of immobility in behavioural despair test

| Compound | Dose, mg/kg | The duration of immobility, sec. |
|---|---|---|
| Control | — | 139.2 ± 5.4 |
| Compound 1 | 5.0 | 117.3 ± 6.9 |
| | 10.0 | 110.8 ± 5.1 |
| Control | — | 166.7 ± 9.4 |

TABLE 5-continued

The influence of compounds on the duration of immobility in behavioural despair test

| Compound | Dose, mg/kg | The duration of immobility, sec. |
|---|---|---|
| Compound 2 | 10.0 | 203.4 ± 14.1$^a$ |
| | 20.0 | 234.9 ± 12.6$^a$ |
| Control | — | 178.4 ± 12.1 |
| Compound 3 | 10.0 | 209.3 ± 6.5$^a$ |
| | 20.0 | 254.6 ± 10.9$^a$ |
| Control | — | 178.4 ± 12.1 |
| Compound 4 | 10.0 | 197.3 ± 5.9 |
| | 20.0 | 202.7 ± 6.7 |
| Control | — | 248.2 ± 7.9 |
| Compound 5 | 10.0 | 189.4 ± 10.3$^a$ |
| | 10.0 | 218.3 ± 12.1 |
| | 20.0 | 216.4 ± 14.2 |
| Control | — | 248.2 ± 7.9 |
| Compound 6 | 1.0 | 184.3 ± 11.7$^a$ |
| | 10.0 | 201.7 ± 13.1 |
| Control | — | 166.7 ± 9.4 |
| Compound 7 | 10.0 | 169.3 ± 11.8 |
| | 20.0 | 147.8 ± 7.1 |

$^a$P < 0.05 compared to control

EXAMPLE 13

Acute Toxicity

The compounds of the present invention were checked for acute toxicity in outbred male mice (18-22 g.). They were administered intraperitoneally and the lethality was estimated 24 hours later (Table 6). In the dose range of 500-1000 mg/kg i.p. Compound 1 caused death in 50% of the animals. Compound 1 is almost 5 times less toxic than other compounds.

TABLE 6

Acute toxicity in mice

| Compound | LD$_{50}$ (mg/kg, i.p.) |
|---|---|
| Compound 1 | 1540 (1385-2716) |
| Compound 2 | 340 (280.7-369.4) |
| Compound 3 | 414 (385.8-442.4) |
| Compound 4 | 105 (77.7-141.7) |
| Compound 5 | 77 (59.2-100.1) |
| Compound 6 | 389 (326.0-452.5) |
| Compound 7 | 115 (82.1-161.0) |

EXAMPLE 14

Antiaggressive Activity

The effect of Compound 1 on the threshold of the aggressive behavior was determined in the experiment on outbred mice (R. Tedesci et al., *J. Pharmacol. Exp. Ther.*, 125, 28-34, (1959), which is incorporated herein by reference). The paired mice were placed on the electrified floor. The strength of the current, which provoked the fighting, was recorded. Compound 1 was demonstrated to be able to enhance the threshold of aggressive response (Table 7).

TABLE 7

The effect of Compound 1 on the threshold of the aggressive behavior in mice

| Compounds | Dose, mg/kg i.p. | Aggression threshold (V) |
|---|---|---|
| Control | — | 32.8 ± 3.7 |
| Compound 1 | 0.5 | 67.2 ± 1.7$^a$ |
| | 5.0 | 90.8 ± 4.9$^b$ |
| Diazepam | 1.0 | 45.4 ± 9.5$^a$ |
| | 5.0 | 92.4 ± 15.6$^b$ |
| Medazepam | 5.0 | 32.2 ± 5.25 |

TABLE 7-continued

The effect of Compound 1 on the threshold of the aggressive behavior in mice

| Compounds | Dose, mg/kg i.p. | Aggression threshold (V) |
|---|---|---|
|  | 10.0 | 43.1 ± 4.2 |

[a]$P < 0.05$
[b]$P < 0.01$

EXAMPLE 15

A Study of the Action of Compound 1 on the Convulsive Effect of Pentylenetetrazole The influence of Compound 1 on the latency of convulsions and on the duration of animals' lives after pentylenetetrazole (130 mg/kg subcutaneously) was studied in outbred mice. It has been demonstrated that Compound 1 causes prolongation of the latency of convulsions and of animal survival after pentylenetetrazole (Table 8).

TABLE 8

Influence of Compound 1 on the convulsive effect of pentylenetetrazole

| Compounds | Dose, mg/kg | Latency of clon. (min.) | Latency of ton. (min.) | Duration of animal survival (min.) |
|---|---|---|---|---|
| Control (pentylenetetrazole) | 130 | 2.22 ± 0.5 | 4.9 ± 1.4 | 5.2 ± 1.4 |
| Compound 1 + pentylenetetrazole | 10 + 130 | 3.35 ± 0.7 | 7.06 ± 1.0 | 7.3 ± 1.0 |

EXAMPLE 16

A Study of Action of Compound 1 on the Open Field Behavior of Inbred Mice

The effects of Compound 1 on different emotional stress reactions (ESR) in male mice of C57 B1/6 and BALB/c strains were studied. ESR indices were evaluated as changes in mice ambulations, defecations and motor activity in an "open field" test (Seredenin S. B., Vedernikov, A. A., Bull. Exp. Biol. Med., 100, No. 7, 38–40 (1979), which is incorporated herein by reference). Compound 1 was injected in different doses intraperitoneally 45 min. before test.

The data obtained showed (Table 9 and 10) that in intact animals the total locomotor activity of C57 B1/6 mice was significantly higher than that of BALB/c animals. Compound 1 in the doses 2.5 and 5.0 mg/kg caused ambulation increase elevating the central activity, and defecation decrease in BALB/c mice. An opposite effect was observed in C57 B1/6 mice: Compound 1 in a dose of 5 mg/kg caused the reduction of total ambulations inhibiting central and vertical activity. The number of defecations was not changed.

Compound 1 is similar to diazepam in terms of manifestation of anxiolytic effect in BALB/c mice demonstrating freezing reaction in an "open field" test. However, there exists a dose, characteristic for Compound 1, in which anxiolytic effect in BALB/c mice does not coincide with sedative effect in C57B 1/6 mice active in "open field" test. Thus, unlike a majority of other tranquilizers, a dissociation of anxiolytic and sedative effects was established for Compound 1.

TABLE 9

The influence of Compound 1 on locomotor activity of BALB/c mice

| Compound, Dose mg/kg | Total locomotor activity | Central activity | Emotionality (N. of defec.) | Crosses of Squires | Vert. stands |
|---|---|---|---|---|---|
| Control | 16.1 ± 3.0 | 0.4 ± 0.2 | 0.93 ± 0.2 | 15.7 ± 3.0 | 01. ± 0.1 |
| Compound 1 |  |  |  |  |  |
| 0.1 | 21.2 ± 5.8 | 0.0 | 0.5 ± 0.17 | 21.2 ± 5.8 | 0.0 |
| 1.0 | 26.1 ± 4.6 | 0.4 ± 0.3 | 1.2 ± 0.13 | 25.6 ± 4.6 | 0.1 ± 0.1 |
| 2.5 | 29.3 ± 5.3[a] | 3.3 ± 2.5 | 0.06 ± 0.06[a] | 25.8 ± 5.2 | 0.2 ± 0.1 |
| 5.0 | 33.0 ± 6.1[a] | 2.4 ± 0.9[a] | 0.45 ± 0.11[a] | 29.8 ± 5.2a | 0.9 ± 0.5[b] |
| 25.0 | 23.1 ± 6.8 | 0.4 ± 0.4 | 0.5 ± 0.17 | 22.7 ± 6.8 | 0.0 |

[a]$P < 0.05$ compared to control
[b]$P < 0.01$ compared to control
[c]$P < 0.001$ compared to control

TABLE 10

The influence of Compound 1 on locomotor activity of C57 B1/6 mice

| Compound, Dose mg/kg | Total locomotor activity | Central activity | Emotionality (No. of defec.) | Crosses of Squires | Vert. stands |
|---|---|---|---|---|---|
| Control | 99.0 ± 9.9 | 20.7 ± 3.8 | 0.61 ± 0.18 | 64.4 ± 5.7 | 14.6 ± 1.7 |
| Compound 1 |  |  |  |  |  |
| 0.1 | 114.6 ± 12.1 | 24.2 ± 5.2 | 1.0 ± 0.53 | 74.6 ± 7.6 | 15.8 ± 2.5 |
| 1.0 | 110.6 ± 10.9 | 29.9 ± 5.2 | 0.8 ± 0.39 | 65.6 ± 5.5 | 15.1 ± 2.0 |
| 2.5 | 114.1 ± 6.0 | 20.1 ± 2.5 | 0.73 ± 0.24 | 74.1 ± 3.9 | 19.9 ± 1.6[a] |
| 5.0 | 71.7 ± 6.9[a] | 11.1 ± 1.6[a] | 0.22 ± 0.22 | 51.7 ± 5.3 | 7.8 ± 1.5[b] |

[a]$P < 0.05$ compared to control
[b]$P < 0.01$ compared to control

EXAMPLE 17

A Study of the Influence of Compound 1 on Memory Formation

The influence of Compound 1 on memory formation was studied in a passive avoidance test, step-through paradigm (equipment of Laffaette Co., USA). The experiments were carried out on outbred male albino rats (180–22 g). Compound 1 and other drugs were administered intraperitoneally 45 min. before the passive avoidance training. The retention was tested 24 hours later learning (painful electroshock in the dark compartment)

by the measurement of the time spent in the dark compartment for 3 min.

Compound 1 was demonstrated to be able to facilitate the learning ability: the time spent in the dark compartment was significantly decreased. Contrary to this, benzodiazepines induced amnesia: increasing values of the time spent in the dark compartment (Table 11).

TABLE 11

Comparative estimation of Compound 1 and benzodiazepines influence on the memory formation in passive avoidance (retention test)

| Compounds | Dose mg/kg, i.p. | The time spent (sec.) in light compartment | in dark compartment |
|---|---|---|---|
| Control | Saline | 141.0 ± 9.2 | 39.0 ± 8.8 |
| Compound 1 | 5.0 | 164.1 ± 9.4[a] | 15.9 ± 3.4[a] |
| Diazepam | 5.0 | 52.3 ± 11.3[a] | 127.7 ± 21.1[a] |
| Medazepam | 5.0 | 37.4 ± 19.5[b] | 142.6 ± 19.58[b] |

[a] $P < 0.05$ compared to control
[b] $P < 0.01$ compared to control

EXAMPLE 18

Estimation of Possible Myorelaxant Effects of Compound 1

The influence of Compound 1 on the motor behavior was studied according to a "rotating rod" test and a "horizontal wire" test in outbred male mice (18–22 g). A rotating rod (2 cm diameter and 5 rpm speed) was used. Acquisition was defined as the ability to remain on the rotating rod for 2 min. Each animal had two trials. According to the "horizontal wire" test a mouse was hung on the wire (0.3 cm. diameter, wire was fixed horizontally 40 cm above the floor) by the forepaws. The ability to pull the hind legs up to the wire for 2 min. was a criterion of test performance.

It was established that Compound 1 in a wide dosage range (5–250 mg/kg) was not able to disturb motor behavior and did not cause myorelaxation (Tabl. 14). Contrary to this, benzodiazepine anxiolytics produced disturbances in coordination of movements and myorelaxation.

TABLE 12

Influence of Compound 1 on the motor behavior (coordination of movements and myorelaxation)

| | | Disturbances according to | | | |
|---|---|---|---|---|---|
| | | Rotating rod test | | Horizontal wire test | |
| Compounds | Dose | Effect in % | ED$_{50}$ mg/kg | Effect in % | ED$_{50}$ mg/kg |
| Compound 1 | 5.0 | 0 | | 0 | |
| | 10.0 | 0 | | 0 | |
| | 20.0 | 0 | | 0 | |
| | 40.0 | 0 | | 0 | |
| | 80.0 | 0 | | 0 | |
| | 250.0 | 0 | | 0 | |
| Diazepam | 1.0 | 25 | | 20 | |
| | 2.0 | 50 | 2.1 (1.2–3.4) | 40 | 2.5 (1.1–6.0) |
| | 5.0 | 80 | | 80 | |
| Medazepam | 2.5 | 40 | | 33 | |
| | 5.0 | 50 | 5.2 (3.7–7.1) | 50 | 7.5 (4.4–12.7) |
| | 10.0 | 96 | | 75 | |

All patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A compound of the following formula:

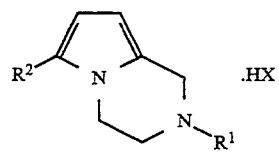

wherein
(a) R$^1$=H;
(b) R$^2$=H; and
(c) HX is succinic acid.

2. A compound of the following formula:

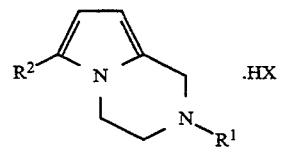

wherein
(a) R$^1$=—C(O)CH$_3$;
(b) R$^2$=—CH$_2$N(CH$_3$)$_2$; and
(c) HX is an acid such that the compound is a therapeutically acceptable acid addition salt.

3. A compound of the following formula:

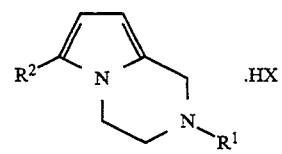

wherein
(a) R$^1$=—C(O)C$_6$H$_5$;
(b) R$^2$=—CH$_2$N(CH$_3$)$_2$; and
(c) HX is an acid such that the compound is a therapeutically acceptable acid addition salt.

* * * * *